(12) United States Patent
Lautar et al.

(10) Patent No.: US 6,303,310 B1
(45) Date of Patent: Oct. 16, 2001

(54) METHOD AND KIT FOR DETECTION OF MULTIPLE PROTEIN INTERACTIONS

(75) Inventors: Susan Lautar, Baltimore; Jie Zhang, Ellicott, both of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 09/359,361

(22) Filed: Jul. 21, 1999

Related U.S. Application Data

(63) Continuation of application No. 08/580,721, filed on Dec. 29, 1995, now abandoned.

(51) Int. Cl.⁷ ............................. C12Q 1/68; G01N 33/53; C12N 1/19; C12N 15/81
(52) U.S. Cl. ........................ 435/6; 435/7.8; 435/254.21; 435/320.1
(58) Field of Search ................................ 435/6, 7.1, 7.8, 435/255.2, 254.21, 320.1

(56) References Cited

U.S. PATENT DOCUMENTS

| | | |
|---|---|---|
| 4,661,454 | 4/1987 | Botstein . |
| 5,013,652 | 5/1991 | Strasberg . |
| 5,139,936 | 8/1992 | Botstein . |
| 5,283,173 * | 2/1994 | Fields et al. ............................. 435/6 |
| 5,306,619 | 4/1994 | Edwards . |
| 5,322,801 | 6/1994 | Kingston . |
| 5,401,629 | 3/1995 | Harpold . |
| 5,432,018 | 7/1995 | Dower . |
| 5,436,128 | 7/1995 | Harpold . |

FOREIGN PATENT DOCUMENTS

| | | |
|---|---|---|
| WO 95/21925 | 8/1995 | (WO) . |

OTHER PUBLICATIONS

Invitrogen Catalog, Apr. 1994, p. 56.*
Osborne et al. (Dec. 1995) The yeast tribid system–genetic detection of trans–phosphorylated ITAM–SH2–interactions. Bio/Technology 13:1474–1478.*
Legrain et al. (Oct. 1993) Interaction between PRP11 and SPP91 yeast splicing factors and characterization of a PRP9–PRP11–SPP91 complex. Science 262:108–110.*
Luban et al. (Feb. 1995) The yeast two–hybrid system for studying protein–protein ineractions. Curr. Opin. Biotechnol. 6:59–64.*
Bartel et al. (1993) Using the two–hybrid system to detect protein–protein interactions. In Hartley (ed.) "Cellular Interaction in Development: A Practical Approach" IRL Press, New York, NY, pp. 153–179.*

* cited by examiner

*Primary Examiner*—Robert A. Schwartzman
(74) *Attorney, Agent, or Firm*—Nixon & Vanderhye P.C.

(57) ABSTRACT

A method and a kit for detecting interactions between three or more proteins, in vivo, using reconstitution of the activity of a transcriptional activator is provided. Reconstitution of the transcriptional activator makes use of chimeric genes which express hybrid proteins. In one embodiment, three types of hybrid proteins are prepared. The first hybrid contains the DNA-binding domain of a transcriptional activator fused to the first test protein. The second hybrid protein contains a transcriptional activation domain fused to the second test protein. The third hybrid protein contains a nuclear localization peptide fused to a third test protein and mediates assembly of the three-protein complex involving the three hybrids. If the three test proteins are able to interact, they bring into close proximity the two domains of the transcriptional activator. This proximity is sufficient to cause transcription, which can be detected by the activity of a marker gene that contains a binding site for the DNA-binding domain.

43 Claims, 5 Drawing Sheets

SEQUENCE LISTING

<160> NUMBER OF SEQ ID NOS: 8

<210> SEQ ID NO 1
<211> LENGTH: 32
<212> TYPE: DNA
<213> ORGANISM: Mus musculus

<400> SEQUENCE: 1
cccctgcagt catgctccaa taaactcact gc                32

<210> SEQ ID NO 2
<211> LENGTH: 33
<212> TYPE: DNA
<213> ORGANISM: Mus musculus

<400> SEQUENCE: 2
tcccccgggg cgaagacgtc acattgttcg aaa                33

<210> SEQ ID NO 3
<211> LENGTH: 28

```
<212> TYPE: DNA
<213> ORGANISM: Mus musculus

<400> SEQUENCE: 3
gaattcttag acgttccggt tcactggg                                          28

<210> SEQ ID NO 4
<211> LENGTH: 29
<212> TYPE: DNA
<213> ORGANISM: Mus musculus

<400> SEQUENCE: 4
cgggatccga agccatcgcc aaatatgac                                         29

<210> SEQ ID NO 5
<211> LENGTH: 30
<212> TYPE: DNA
<213> ORGANISM: Mus musculus

<400> SEQUENCE: 5
ggggatcctc attgaggagt tttctgcatt                                        30

<210> SEQ ID NO 6
<211> LENGTH: 30
<212> TYPE: DNA
<213> ORGANISM: Mus musculus

<400> SEQUENCE: 6
cccccgggga agactttctt cagctcatgt                                        30

<210> SEQ ID NO 7
<211> LENGTH: 151
<212> TYPE: DNA
<213> ORGANISM: Mus musculus
<220> FEATURE:
<221> NAME/KEY: CDS
<222> LOCATION: (1)..(51)

<400> SEQUENCE: 7 atg gat aaa gcg gaa tta att ccc gag cct cca aaa aag aag aga aag       48
Met Asp Lys Ala Glu Leu Ile Pro Glu Pro Pro Lys Lys Lys Arg Lys
 1               5                  10                  15 gtc gaattgggta ccgagctcgg atccactagt aacggccgcc agtgtgctgg              101
Val aattctgcag atatccatca cactggcggc cgctcgagca tgcatctaga                  151

<210> SEQ ID NO 8
<211> LENGTH: 17
<212> TYPE: PRT
<213> ORGANISM: Mus musculus

<400> SEQUENCE: 8

Met Asp Lys Ala Glu Leu Ile Pro Glu Pro Pro Lys Lys Lys Arg Lys
 1               5                  10                  15
Val
```

METHOD AND KIT FOR DETECTION OF MULTIPLE PROTEIN INTERACTIONS

This application is a continuation application of U.S. patent application Ser. No. 08/580,721 filed Dec. 29, 1995, abandoned the entire contents of which are hereby incorporated in their entirety.

BACKGROUND OF THE INVENTION

1. Field of the Invention

The present invention relates to a method for detecting the interaction of three or more proteins in an in vivo system through the use of fused genes encoding hybrid proteins.

2. Description of the Related Art

A fundamental area of inquiry in biology is the analysis of interactions between proteins. Proteins are complex macromolecules made up of covalently linked chains of amino acids. Each protein assumes a unique three dimensional shape determined principally by its sequence of amino acids. Many proteins consist of smaller units termed domains, which are continuous stretches of amino able to fold independently from the rest of the protein. Some of the important forms of proteins are as enzymes, polypeptide hormones, nutrient transporters, structural components of the cell, hemoglobins, anti-bodies, nucleoproteins, and components of viruses.

Multiple protein interactions require three or more proteins to associate. A large number of non-covalent bonds form between the proteins when three or more protein surfaces are precisely matched, and these bonds account for the specificity of recognition. Multiple-protein interactions are involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to the neoplastic transformation through multiple-protein interactions. For example, some oncogenes encode protein kinases whose enzymatic activity on cellular target proteins leads to the cancerous state. Another example of a protein-protein interaction occurs when a virus infects a cell by recognizing a polypeptide receptor on the surface, and this interaction has been used to design antiviral agents.

Protein-protein interactions have been generally studied in the past using biochemical techniques such as crosslinking, co-immunoprecipitation and co-fractionation by chromatography. A disadvantage of these techniques is that interacting proteins often exist in very low abundance and are, therefore, difficult to detect. Another major disadvantage is that these biochemical techniques involve only the proteins, not the genes encoding them. When an interaction is detected using biochemical methods, the newly identified protein often must be painstakingly isolated and then sequenced to enable the gene encoding it to be obtained. Another disadvantage is that these methods do not immediately provide information about which domains of the interacting proteins are involved in the interaction. Another disadvantage is that small changes in the composition of the interacting proteins cannot be tested easily for their effect on the interaction.

There is evidence that transcription can be activated through the use of two functional domains of a transcription factor: a domain that recognizes and binds to a specific site on the DNA and a domain that is necessary for activation, as reported by Keegan, et al., Science, 231, 699–704 (1986) and Ma and Ptashne, Cell, 48, 847–853 (1987). The transcriptional activation domain is thought to function by contracting other proteins involved in transcription. The DNA-binding domain appears to function to position the transcriptional activation domain on the target gene which is to be transcribed. In a few cases now known, these two functions (DNA-binding and activation) reside on separate proteins. One protein binds to the DNA, and the other protein, which activates transcription, binds to the DNA-bound protein, as reported by McKnight et al., Proc. Natl. Acad. Sci. USA, 89, 7061–7065 (1987); another example is reviewed by Curran et al., Cell, 55, 395–397 (1988).

Transcriptional activation has been studied using the GAL4 protein of the yeast *Saccharomyces cerevisiae*. The GAL4 protein is a transcriptional activator required for the expression of genes encoding enzymes of galactose utilization, see Johnston, Microbiol. Rev., 51, 458–476 (1987). It consists of an N-terminal domain which binds to specific DNA sequences designated $UAS_G$ (UAS stands for upstream activation site, G indicates the galactose genes) and a C-terminal domain containing acidic regions, which is necessary to activate transcription, see Keegan et al. (1986), supra, and Ma and Ptashne. (1987), supra. As discussed by Keegan et al., the N-terminal domain binds to DNA in a sequence-specific manner but fails to activate transcription. The C-terminal domain cannot activate transcription because it fails to localize to the $UAS_G$ see for example, Brent and Ptashne, Cell, 43, 729–736 (1985). However, Ma and Ptashne have reported (Cell, 51, 113–119 (1987); Cell, 55, 443–446 (1988)) that when both the GAL4 N-terminal domain and C-terminal domain are fused together in the same protein, transcriptional activity is induced. Other proteins also function as transcriptional activators via the same mechanism. For example, the GCN4 protein of *Saccharomyces cerevisiae* as reported by Hope and Struhl, Cell, 56, 885–894 (1986), the ADR1 protein of *Saccharomyces cerevisiae* as reported by Thukral et al., Molecular and Cellular Biology. 9, 2360–2369, (1989) and the human estrogen receptor, as discussed by Kumar et al. Cell, 51, 941–951 (1987) both contain separable domains for DNA binding and for maximal transcriptional activation.

Recently, protein-protein interactions have been studied using the widely used yeast two-hybrid systems of Fields et al., Nature 340, 245–246 (1989), also disclosed in U.S. Pat. No. 5,283,173 by Fields et al. The yeast two-hybrid system detects binary (X/Y) interactions between proteins through functional reconstitution of transcription factor GAL4 by associating two fusion proteins, GAL4-DNA binding domain, (BD)-X, and GAL4-activation domain, (AD)-Y. Thus, the yeast two-hybrid system offers a sensitive genetic selection method to detect and clone physically interactive proteins. Fields et al., Nature 340, 245–246 (1989); Fields et al., Proc. Natl. Acad. Sci. 88, 9578–9582.

However, the two-hybrid system is limited so far as to detect protein interactions involving two components only. The two-hybrid system cannot detect protein (Z) mediated interactions between proteins (X/Y) where the proteins indirectly interact, e.g. X does not contact Y. The two-hybrid system also cannot detect protein interactions which require modification of the X or Y protein by the Z protein to interact, or have complex conformational requirements for interaction. None of the aforementioned articles suggests a genetic system to detect three or more protein interactions in vivo using transcriptional activation as an assay.

A genetic system that is capable of rapidly detecting which of multiple proteins interact with a known protein, determining which of multiple domains of the proteins interact, and providing the genes for the newly identified interacting proteins has not been available prior to the present invention.

Accordingly, to avoid the disadvantages inherent in the biochemical techniques for detecting multiple protein interactions, it would be desirable to have a method for detecting three or more protein interactions using a genetic system. The genetic system described here is based on transcriptional activation. Transcription is the process by which RNA molecules are synthesized using a DNA template. Transcription is regulated by specific sequences in the DNA which indicate when and where RNA synthesis should begin. These sequences correspond to binding sites for proteins, designated transcription factors, which interact with the enzymatic machinery used for the RNA polymerization reaction.

SUMMARY OF THE INVENTION

The present invention provides a method and a kit for detecting interactions between three or more proteins, in vivo, using reconstitution of the activity of a transcriptional activator. This reconstitution makes use of the chimeric genes which express hybrid proteins. In one embodiment, three types of hybrid proteins are prepared. The first hybrid contains the DNA-binding domain of a transcriptional activator fused to the first test protein. The second hybrid contains a transcriptional activation domain fused to a second test protein. The third hybrid contains a nuclear localization peptide fused to a third test protein. If the three test proteins are able to interact, they bring into close proximity the two domains of the transcriptional activator. This proximity is sufficient to cause transcription, which can be detected by the activity of a marker gene that contains a binding site for the DNA-binding domain.

One advantage of this method is that a multiplicity of proteins can be quickly and simultaneously tested to determine whether any interact with proteins known to be within a protein mediated signal transduction pathway. For example, in a system where three proteins interact, such as X, Y, and Z, but where X and Y do not interact directly and interact only through mediation by Z, a DNA library may be screened and DNA fragments encoding such mediator proteins can yield a positive result. In such an example, a DNA fragment encoding the DNA-binding domain is fused to a DNA fragment encoding the known protein in order to provide one hybrid. A second DNA fragment, encoding the transcriptional activation domain, is fused to a DNA fragment encoding a second protein and provides the second hybrid which indirectly interacts with the first hybrid. These hybrids are introduced into the cells carrying the marker gene. For the third hybrid, a library of plasmids can be constructed which may include, for example, total mammalian complementary DNA (cDNA) to encode the third mediating protein. This library is introduced into the cells carrying the first and second hybrids. If any individual plasmid from the library encodes a protein that is capable of interacting with the known proteins, a positive signal may be obtained. For example, the EGFR/Grb2/Sos system described herein can be easily adapted to screen a pDela plasmid cDNA library to look for Grb2-like adaptor proteins. In addition, when an interaction between proteins occurs, the gene for the newly identified protein is readily available rendering sequencing of the newly identified protein unnecessary.

The system can be used to screen for drugs that disrupt the three hybrid complex and turn off β-galactosidase production within the host cell. Such drugs may either turn off, down-regulate, or up-regulate signal transduction pathways, e.g. intervening in the tyrosine receptor signal transduction pathway that has been implied in certain pathological conditions such as adenocarcinoma. Also, drugs regulating complex pathways such as protein synthesis, protein modification, protein catabolism, cellular regulation, and the like, can be detected.

The system can be of value in the identification of new genes. For example, receptors on the cell surface may be identified for known growth factors, toxins, or surface antigens. Proteins that interact with oncogene-encoded products may be discovered, and these proteins can be of therapeutic value.

The system can be used in the design of peptide inhibitors. For example, peptides that interact with enzymes such as proteases or kinases can be identified and then tested in other systems for their ability to inhibit the enzymatic reaction. Peptides that bind to bacterial or viral proteins can be identified and then tested in other systems for their ability to inhibit these bacteria or viruses.

The system can be used to test affinity reagents for protein purification. Pepzides or protein domains can be identified that interact with the known protein of interest and these may then be used in a purification protocol for the known protein.

A broad embodiment of the present invention encompasses a method for detecting multiple protein interactions, the method comprising:

(a) providing a host cell containing a detectable gene wherein the detectable gene expresses a detectable protein when the detectable gene is activated by an amino acid sequence including a transcriptional activation domain when the transcriptional activation domain is in sufficient proximity to the detectable gene;

(b) providing a first chimeric gene that is capable of being expressed in the host cell, the first chimeric gene comprising a DNA sequence that encodes a first hybrid protein, the first hybrid protein comprising:
  (i) a DNA-binding domain that recognizes a binding site on the detectable gene in the host cell; and
  (ii) a first test protein or fragment thereof that is to be tested for interaction with a second test protein or fragment thereof and at least one mediating test protein or fragment thereof;

(c) providing a second chimeric gene that is capable of being expressed in the host cell, the second chimeric gene comprising a DNA sequence that encodes a second hybrid protein, the second hybrid protein comprising:
  (i) the transcriptional activation domain; and
  (ii) a second test protein or fragment thereof that is to be tested for interaction with the first test protein or fragment thereof and with at least one mediating test protein or fragment thereof;

(d) providing at least one mediating chimeric gene that is capable of being expressed in the nuclei of the host cell, each mediating chimeric gene comprising a DNA sequence that encodes a mediating hybrid protein, the mediating hybrid protein comprising:
  (i) a nuclear localization peptide; and
  (ii) a mediating test protein or fragment thereof that is to be tested for interaction with the first test protein or fragment thereof and the second test protein or fragment thereof;

wherein interaction between the first test protein, the second test protein, and the mediating test protein in the host cell causes the transcriptional activation domain to activate transcription of the detectable gene;
(e) introducing the first chimeric gene, the second chimeric gene, and the mediating chimeric gene into the host cell;
(f) subjecting the host cell to conditions under which the first hybrid protein, the second hybrid protein, and the mediating hybrid protein are expressed in sufficient quantity for the detectable gene to be activated; and,
(g) determining whether the detectable gene has been expressed to a degree greater than expression in the absence of an interaction between the first test protein, the second test protein, and the mediating test protein.

An alternate embodiment of the present invention provides a method for detecting an interaction between a first test protein, a second test protein, and a third test protein, the method comprising:
(a) providing a yeast host cell containing a detectable gene wherein the detectable gene expresses a detectable protein when the detectable gene is activated by an amino acid sequence including a transcriptional activation domain when the transcriptional activation domain is in sufficient proximity to the detectable gene;
(b) providing a first chimeric gene that is capable of being expressed in the host cell, the first chimeric gene comprising a DNA sequence that encodes a first hybrid protein, the first hybrid protein comprising:
   (i) a DNA-binding domain that recognizes a binding site on the detectable gene in the host cell; and
   (ii) a first test protein or fragment thereof that is to be tested for interaction with a second test protein or fragment thereof and at least one third test protein or fragment thereof;
(c) providing a second chimeric gene that is capable of being expressed in the host cell, the second chimeric gene comprising a DNA sequence that encodes a second hybrid protein, the second hybrid protein comprising:
   (i) the transcriptional activation domain; and
   (ii) a second test protein or fragment thereof that is to be tested for interaction with the first test protein or fragment thereof and the third test protein or fragment thereof;
(d) providing a third chimeric gene that is capable of being expressed in the nuclei of the host cell, the third chimeric gene comprising a DNA sequence that encodes a third hybrid protein, the third hybrid protein comprising:
   (i) a nuclear localization peptide; and
   (ii) a third test protein or fragment thereof that is to be tested for interaction with the first test protein or fragment thereof and the second test protein or fragment thereof;
   wherein interaction between the first test protein, the second test protein, and the third test protein in the host cell causes the transcriptional activation domain to activate transcription of the detectable gene;
(e) introducing the first chimeric gene, the second chimeric gene, and the third chimeric gene into the host cell;
(f) subjecting the host cell to conditions under which the first hybrid protein, the second hybrid protein, and the third hybrid protein are expressed in sufficient quantity for the detectable gene to be activated; and,
(g) determining whether the detectable gene has been expressed to a degree greater than expression in the absence of an interaction between the first test protein, the second test protein, and the third test protein.

A preferred embodiment of the present invention provides a method for detecting an interaction between a first test protein, a second test protein, and a third test protein, the method comprising:
(a) providing a Saccharomyces cerevisiae host cell containing a GAL1-lacZ gene wherein the GAL1-lacZ gene expresses a β-galactosidase protein when the GAL1-lacZ gene is activated by an amino acid sequence including a transcriptional activation domain of yeast transcription factor GAL4 when the transcriptional activation domain is in sufficient proximity to the GAL1-lacZ gene, and containing a GAL1-His3 gene, when the GAL1-His3 gene is activated providing histidine-independent yeast growth;
(b) providing a first DNA plasmid, the first DNA plasmid comprising a first chimeric gene that is capable of being expressed in the host cell, the first chimeric gene comprising a DNA sequence that encodes a first hybrid protein, the first hybrid protein comprising:
   (i) a DNA-binding domain of yeast transcription factor GAL4 that recognizes a binding site on the GAL1-lacZ gene in the host cell; and
   (ii) a first test protein or fragment thereof that is to be tested for interaction with a second test protein or fragment thereof and at least one third test protein or fragment thereof;
(c) providing a second DNA plasmid, the second DNA plasmid comprising a second chimeric gene that is capable of being expressed in the host cell, the second chimeric gene comprising a DNA sequence that encodes a second hybrid protein, the second hybrid protein comprising:
   (i) the transcriptional activation domain; and
   (ii) a second test protein or fragment thereof that is to be tested for interaction with the first test protein or fragment thereof and the third test protein or fragment thereof;
(d) providing a third DNA plasmid, the third DNA plasmid comprising a third chimeric gene that is capable of being expressed in the nuclei of the host cell, the third chimeric gene comprising a DNA sequence that encodes a third hybrid protein, the third hybrid protein comprising:
   (i) an SV40 T antigen nuclear localization peptide sequence; and
   (ii) a third test protein or fragment thereof that is to be tested for interaction with the first test protein or fragment thereof and the second test protein or fragment thereof;
   wherein interaction between the first test protein, the second test protein, and the third test protein in the host cell causes the transcriptional activation domain to activate transcription of the GAL-lacZ gene;
(e) introducing the first DNA plasmid, the second DNA plasmid, and the third DNA plasmid into the host cell;
(f) subjecting the host cell to conditions under which the first hybrid protein, the second hybrid protein, and the third hybrid protein are expressed in sufficient quantity for the GAL-lacZ gene to be activated; and,
(g) determining whether the GAL1-lacZ gene has been expressed to a degree greater than expression in the absence of an expression of the first test protein, or the second test protein, or the third test protein.

In another preferred embodiment of the present invention, a kit is provided for detecting interaction between a first test protein and a second test protein where the proteins interact through mediation by one or more third proteins, the kit comprising:
(a) a container;

(b) a host cell is provided within the container, the host cell contains a detectable gene having a binding site for a DNA-binding domain of a first hybrid protein, the binding site positioned so that the detectable gene expresses a detectable protein when the detectable gene is activated by a transcriptional activation domain encoded by a second vector, activation of the detectable gene occurs when the transcriptional activation domain is in sufficient proximity to the detectable gene, the host cell, by itself, incapable of expressing a protein having a function of a first marker gene, a second marker gene, the DNA-binding domain, or the transcriptional activation domain;

(c) a first vector is provided within the container, the first vector contains a promoter and a transcription termination signal functionally associated with a first chimeric gene in order to direct the transcription of the first chimeric gene, the first chimeric gene includes a DNA sequence that encodes a DNA-binding domain and at least one unique restriction site for inserting a DNA sequence encoding a first test protein or protein fragment in such a manner that the first test protein is expressed as part of a hybrid protein with the DNA-binding domain, the first vector also includes a means for self-replicating in the host cell, a first marker gene, the expression of which in the host cell permits selection of cells containing the first marker gene from cells that do not contain the first marker gene;

(d) a second vector is provided within the container, the second vector contains a second chimeric gene, the second chimeric gene includes a promoter and a transcription termination signal to direct transcription, the second chimeric gene also includes a DNA sequence that encodes a transcriptional activation domain and at least one unique restriction site to insert a DNA sequence encoding a second test protein or protein fragment into the vector, such that the second test protein is capable of being expressed as part of a hybrid protein with the transcriptional activation domain, the second vector further includes a means for self-replicating in the host cell, a second marker gene, the expression of which in the host cell permits selection of cells containing the second marker gene from cells that do not contain the second marker gene; and, (e) a third vector is provided within the container, the third vector contains a third chimeric gene, the third chimeric gene includes a promoter and a transcription termination signal to direct transcription, the third chimeric gene includes at least one unique restriction site to insert a DNA sequence encoding a third test protein or protein fragment into the vector in such a manner that the third test protein is capable of being expressed as part of a hybrid protein, the third vector also includes a means for self-replicating in the host cell, a nuclear localization peptide, and a third marker gene, the expression of which in the host cell permits selection of cells containing the third marker gene from cells that do not contain the third marker gene.

DETAILED DESCRIPTION OF THE INVENTION

Figure 1:
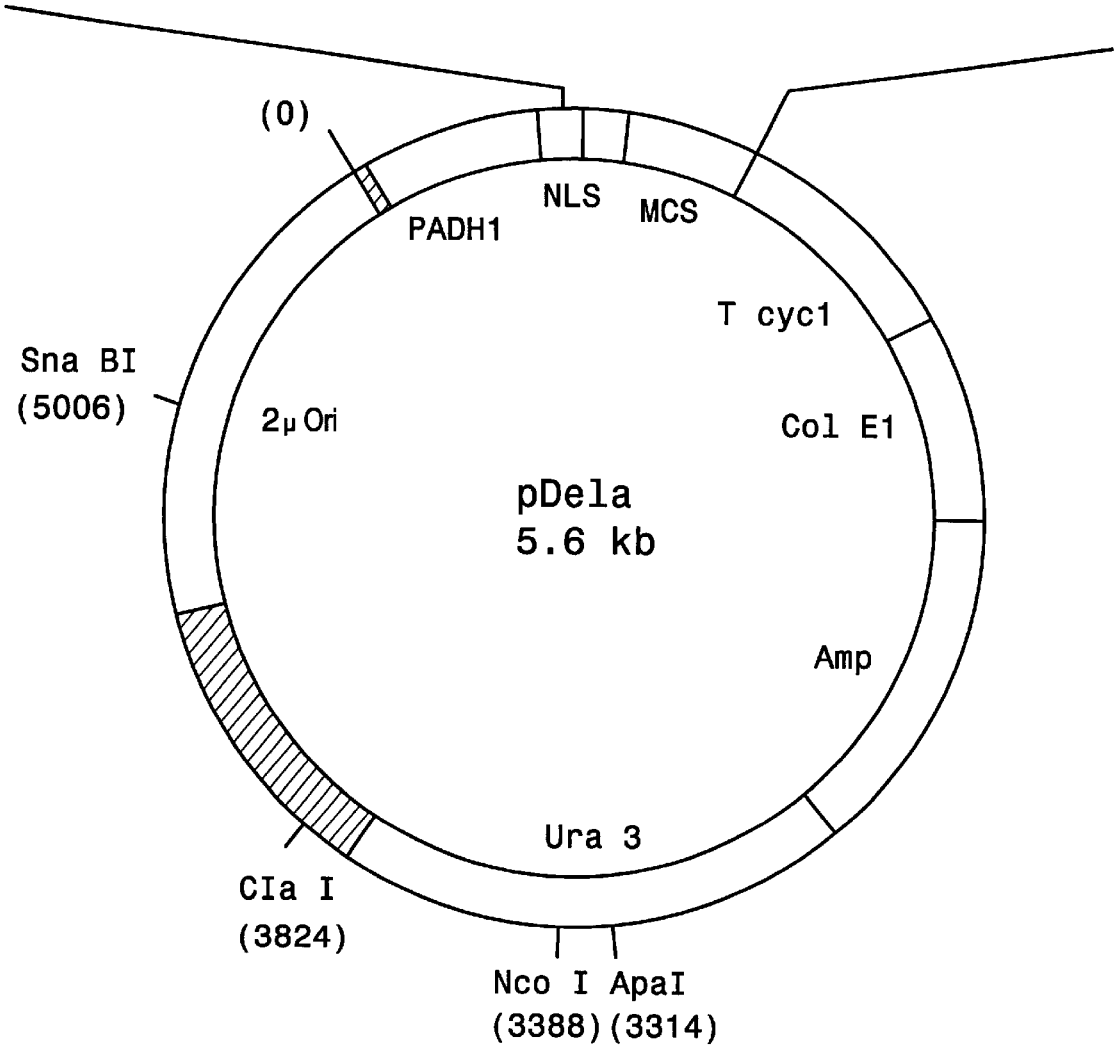
FIG. 1 is a representational map of the plasmid pDela for expression of a third protein-hybrid in yeast nuclei and shows SEQ ID NO: 7 and SEQ ID NO: 8 as an insert.

A method for detecting the interaction between three or more test proteins is provided in accordance with the present invention. The method includes providing a host cell, preferably a yeast cell, most preferably *Saccharomyces cerevisiae* or *Schizosaccharomyces pombe*. The host cell contains a detectable gene having a binding site for the DNA-binding domain of the transcriptional activator, such that the detectable gene expresses a detectable protein when the detectable gene is transcriptionally activated. Such activation occurs when the transcriptional activation domain of a transcriptional activator is brought into sufficient proximity to the DNA-binding domain of the transcriptional activator.

A first chimeric gene is provided which is capable of being expressed in the host cell. The first chimeric gene may be present in a chromosome of the host cell. The first chimeric gene comprises a DNA sequence that encodes a first hybrid protein. The first hybrid protein contains a DNA-binding domain that recognizes the binding site on the detectable gene in the host cell. The first hybrid protein contains a first test protein or protein fragment which is to be tested for interaction with a second test protein or protein fragment and a third test protein or protein fragment. In one preferred embodiment, the first hybrid is carried on the pGBT9 plasmid.

A second chimeric gene is provided which is capable of being expressed in the host cell. In one embodiment, the first, second and third chimeric genes are introduced into the host cell in the form of plasmids. Preferably, one chimeric gene is present in a chromosome of the host cell and the other chimeric genes are introduced into the host cell as part of a plasmid or plasmids. In a preferred embodiment, the second hybrid is on the pGAD424 plasmid.

The second chimeric gene contains a DNA sequence that encodes a second hybrid protein. The second hybrid protein contains a transcriptional activation domain. The second hybrid protein also contains a second test protein or a protein fragment which is to be tested for interaction with the first and third test proteins or protein fragments. Preferably, the DNA-binding domain of the first hybrid protein and the transcriptional activation domain of the second hybrid protein are derived from transcriptional activators having separate DNA-binding and transcriptional activation domains. These separate DNA-binding and transcriptional activation domains are also known to be found in the yeast GAL4 protein, and are also known to be found in the yeast GCN4 and ADR1 proteins. Many other proteins involved in transcription also have separable binding and transcriptional activation domains which make them useful for the present invention. In another embodiment, the DNA-binding domain and the transcriptional activation domain may be from different transcriptional activators.

The third chimeric gene contains a DNA sequence that encodes a third hybrid protein or protein fragment. In a preferred embodiment, the DNA sequence is constructed on a plasmid (pDela) which is compatible with two widely used plasmids, e.g. pGBT9 and pGAD424. Most of the currently used two-hybrid plasmids, e. g. pGBT9 and pGAD424, employ Leu$^+$ and Trp$^+$ genes as selection markers for maintaining them in Leu$^-$ Trp$^-$ yeast strains. In one embodiment, the plasmid encoding the third hybrid protein also contains a selection marker gene, e.g. Ura3$^+$, so that triple transformants of the hybrid plasmids, e.g. pDela, pGBT9 and pGAD424, can be selected on an appropriate yeast background, e.g. Ura$^-$Trp$^-$Leu$^-$. High level constitutive transcription of the third hybrid is driven by an appropriate strong promoter, such as that of house-keeping alcohol dehydrogenase gene 1 (PADH1). Preferably, the third hybrid protein is targeted to yeast nuclei by a nuclear localization signal, e.g. the SV40 T antigen NLS sequence. The third hybrid protein may also be encoded on a library of plasmids that contain genomic, cDNA or synthetically generated DNA sequences fused to the DNA sequence encoding the nuclear localization sequence.

The interaction between the three test proteins in the host cell, therefore, causes the transcriptional activation domain to activate transcription of the detectable gene. The method is carried out by introducing the three chimeric genes into the host cell. The host cell is subjected to conditions under which the hybrid proteins are expressed in sufficient quantity for the detectable gene to be activated. The cells are then tested for their expression of the detectable gene to be a greater degree than in the absence of an interaction between the three test proteins.

Thus, interactions between two indirectly interacting test proteins and mediating proteins can be tested. For example, the test proteins may be derived from bacterial proteins, viral proteins, oncogene-encoded proteins, growth factors or an enzymes. The third test protein may be derived from a library of plasmids as described above.

The method of the present invention, as described above, may be practiced using a kit for detecting interaction between a first test protein and a second test protein where the proteins interact through mediation by one or more "third" proteins. The kit includes a container, three vectors, and a host cell. The first vector contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding a first test protein or protein fragment in such a manner that the first test protein is expressed as part of a hybrid protein with the DNA-binding domain. The first vector also includes a means for replicating itself in the host cell and in bacteria. Also included on the first vector is a first marker gene, the expression of which in the host cell permits selection of cells containing the first marker gene from cells that do not contain the first marker gene. Preferably, the first vector is plasmid such as pGBT9.

The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second test protein or protein fragment into the vector, in such a manner that the second test protein is capable of being expressed as part of a hybrid protein with the transcriptional activation domain. Preferably, the DNA-binding domain of the first hybrid protein and the transcriptional activation domain of the second hybrid protein are derived from transcriptional activators having separate DNA-binding and transcriptional activation domains. These domains are known to be found in the yeast GAL4 protein, and are also known to be found in the yeast GCN4 and ADR1 proteins. Many other proteins involved in transcription also have separable binding and transcriptional activation domains which make them useful for the present invention. In another embodiment, the DNA binding domain and the transcriptional activation domain may be from different transcriptional activators. The second vector further includes a means for replicating itself in the host cell and in bacteria. The second vector also includes a second marker gene, the expression of which in the host cell permits selection of cells containing the second marker gene from cells that do not contain the second marker gene.

The kit also provides a third vector, which contains a third chimeric gene. The third chimeric gene also includes a promoter and a transcription termination signal to direct transcription. The third chimeric gene includes a unique restriction site(s) to insert a DNA sequence encoding the third test protein or protein fragment into the vector in such a manner that the third test protein is capable of being expressed as part of a hybrid protein. The third hybrid protein may be encoded on a library of plasmids DNA sequences fused to the DNA sequence encoding the nuclear localization sequence. The third vector also includes a means for replicating itself in the host cell and in bacteria. The third vector includes a nuclear localization peptide, such as SV40 T antigen nuclear localization sequence, and a second marker gene, the expression of which in the host cell permits selection of cells containing the third marker gene from cells that do not contain the third marker gene.

The kit includes a host cell, preferably a yeast strain of *Saccharomyces cerevisiae* or *Schizosaccharomyces pombe*. The host cell contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene. The host cell, by itself, is incapable of expressing a protein having a function of the first marker gene, the second marker gene, the third marker gene, the DNA-binding domain, or the transcriptional activation domain.

Due to the interaction of the test proteins in the host cell, use of the kit provides a measurably greater expression of the detectable gene than in the absence of an interaction between the test proteins. The detectable gene may encode an enzyme or other product that can be readily measured. Such measurable activity may include the ability of the cell to grow only when the marker gene is transcribed, or the presence of detectable enzyme activity only when the marker gene is transcribed. Various other markers are well known within the skill of workers in the art.

The cells containing the three hybrid proteins are incubated in a appropriate medium and the culture is monitored for the measurable activity. A positive test for this activity is an indication that the test proteins have interacted. Such interaction between the multiple proteins brings their respective DNA-binding and transcriptional activation domains into sufficiently close proximity to cause transcription of the marker gene.

The basic strategy of the testing method includes preparing the system of three hybrid proteins containing domains of a yeast transcriptional activator, as described. The first hybrid contains the DNA-binding domain of a transcriptional activator fused to the first test protein. The second hybrid protein contains a transcriptional activation domain fused to the second test protein. The third hybrid protein mediates assembly of the three-protein complex involving the three hybrids. If the three test proteins are able to interact, they bring into close proximity the two domains of the transcriptional activator. This proximity is sufficient to cause transcription, which can be detected by the activity of a marker gene that contains a binding site for the DNA-binding domain. A yeast strain, e.g. BY1361, is used that carries several genes under the regulation of $UAS_G$ and therefore to bind the GAL4 DNA-binding domain. One of these genes is GAL1-lacZ, which contains the E. coli lacZ gene encoding β-galactosidase. X-gal is an abbreviation for 5-bromo-4-chloro-3-indolyl-β-D-galactopyranoside. X-gal is cleaved by β-galactosidase, producing a color change. Therefore β-galactosidase activity, detected by liquid assay or by colony color on appropriate media, is a measure of GAL4 function. Furthermore, mere growth of the yeast on galactose requires the transcription of genes regulated by GAL4 and is also a measure of GAL4 function. The host yeast strain carries a deletion of the chromosomal GAL4 gene, such that any GAL4 function must be due to that encoded by the introduced plasmids.

Figure 3A:
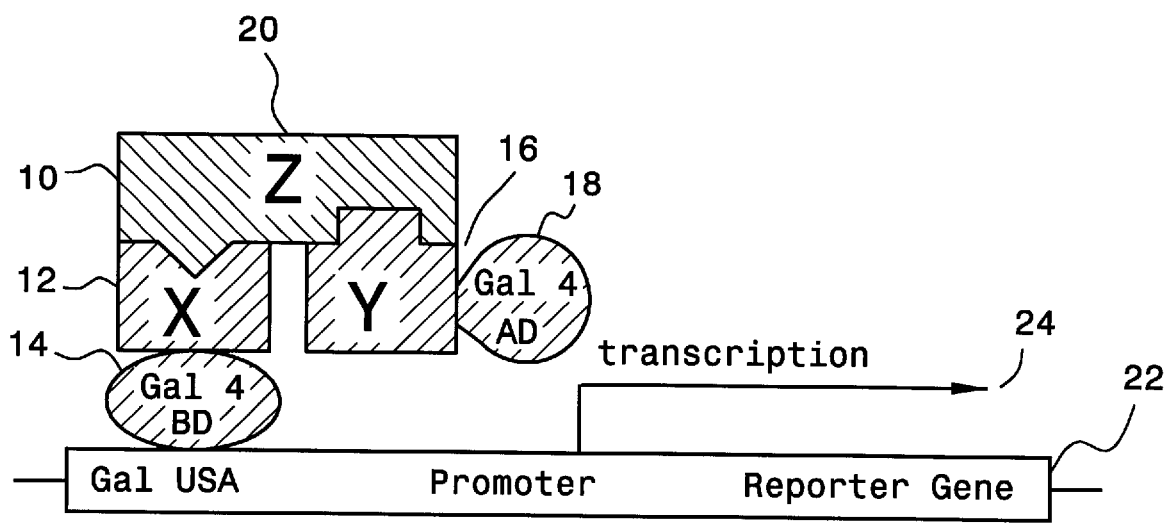
FIG. 3A is a schematic representations of the three-hybrid system where interaction of proteins X and Y requires mediation by protein Z to reconstitute transcriptional activation of GAL4 activity.
Figure 3B:
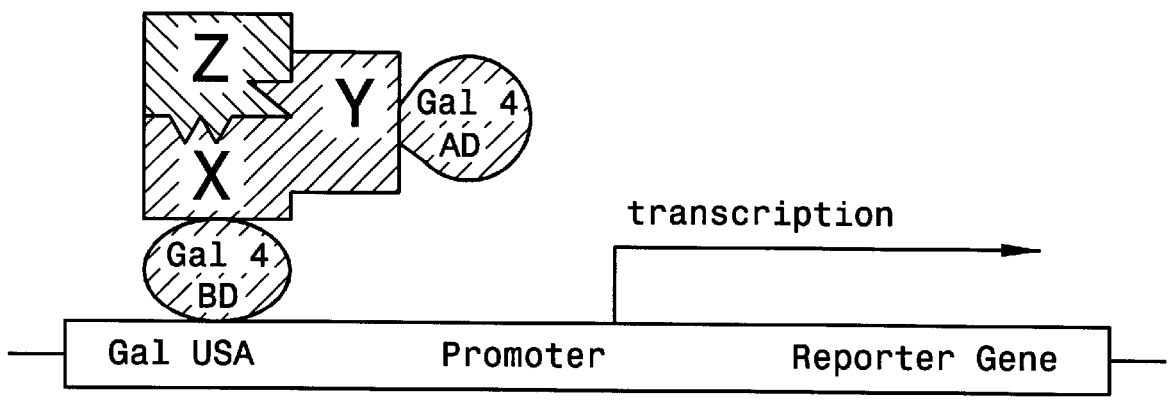
FIG. 3B is a schematic representation of the three-hybrid system where protein Y only binds to a new composite contour created by the combination of protein X and protein Z to achieve reconstitution of GAL4 transcriptional activation.
Figure 3C:
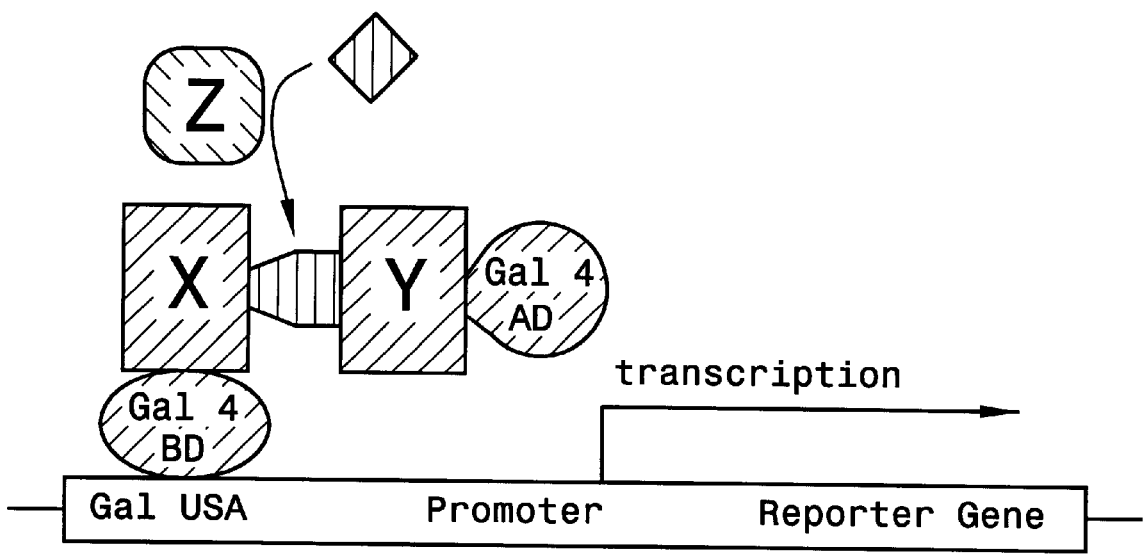
FIG. 3C is a schematic representation of the three-hybrid system where Y binds to X only after X is modified by Z to achieve reconstitution of GAL4 transcriptional activation.

The genetic aspect of the testing method is shown in FIG. 3. FIG. 3A schematically illustrates GAL4-hybrid complex 10 showing the binding of the GAL4-first hybrid fusion protein 12 having a DNA-binding domain 14. The GAL4-second hybrid fusion protein 16 is shown having a transcriptional activation domain 18. The third hybrid protein 20 is shown mediating the protein interaction which supplies the proper placement of the binding domain and the transcriptional activation domain. The GAL4-hybrid complex 10, containing both domains 14 and 18, provides potent activation of transcription of the GAL1-lacZ gene 22 when yeast are grown on galactose media. Transcription of the GAL1-lacZ gene 22 is indicated by the arrow 24. None of these hybrid proteins 12, 16 or 20, alone, is able to activate transcription. The interaction of proteins X, Y and Z, as illustrated in FIGS. 3A–C, allows the portion of the GAL4 activation domain 18 to be brought into sufficient proximity to the DNA-binding domain 14 of GAL4, allowing transcription 24 of GAL1-lacZ gene 22 to occur. Transcriptional activation can be determined by measuring β-galactosidase activity when the yeast are grown on galactose containing media.

The system is dependent on a number of conditions to properly carry out the method of this invention. The first interacting protein X must not, itself, carry as activation domain for the marker. Otherwise the activation domain would allow transcription of the marker gene as soon as the vector encoding only the GAL4 DNA-binding domain fused to the first interacting protein X is introduced. The interaction between the first test protein X and the second or third test protein Y, protein Z must be capable of occurring within the yeast nucleus. The GAL4 activation domain portion of the hybrid containing the second test protein Y must be accessible to the transcription machinery of the cell to allow transcription of the marker gene. Should any of these conditions not exist, the system may be modified for use by constructing hybrids that carry only portions of the interacting proteins X Y, and Z, and thus meet these conditions.

This system can be used to genetically select for proteins that mediate interactions of known proteins, provided the gene encoding the known proteins are available. Yeast containing the known proteins as a hybrid with the GAL4 DNA activation domain and GAL4 DNA-binding domain can be transformed with a clone bank of genomic or CDNA sequences fused to the nuclear localization domain. The triple transformants can be selected for their ability to grow on histidine drop-out media, or screened for blue color on indicator plates for those transformants able to express the GAL1-lacZ fusion.

Since other eukaryotic cells use a mechanism similar to that of yeast for transcription, other eukaryotic cells such as HeLa cells can be used instead of yeast to test for multiple protein interactions. The reporter gene function can be served by any of a large variety of genes, such as genes encoding drug resistance or metabolic enzymes. The function of GAL4 can be served by any transcriptional activator that has separable domains for DNA-binding and for transcriptional activation. Indeed, any protein, even one that is not a transcriptional activator, that has two separable functions can be used to establish a similar genetic system to detect multiple-protein interactions.

Accordingly, the method of the present invention can be applied more generally to any detectable function requiring separable domains of an amino acid sequence which can be reconstituted. This general embodiment of the present invention detects interaction between three test proteins. The method includes providing a host cell which is defective in a detectable function requiring three protein interaction. The detectable function is provided by an amino acid sequence having separable domains. Thus, the amino acid sequence includes a first domain and a second domain which are capable of producing the detectable function when they are brought together by a third hybrid protein in sufficient proximity to each other in the host cell.

In such a general application, chimeric genes are provided that are capable of being expressed in the host cell. The first chimeric gene includes a DNA sequence that encodes a first hybrid protein. The first hybrid protein contains the first domain of the amino acid sequence. The first hybrid protein also contain a first test protein or protein fragment which is to be tested for interaction with a second test protein or protein fragment and a third test protein or protein fragment.

A second chimeric gene is provided which is capable of being expressed in the host cell. The second chimeric gene contains a DNA sequence that encodes a second hybrid protein. The second hybrid protein contains the second domain of the amino acid sequence. The second hybrid protein also contains a second test protein or protein fragment which is to be tested for interaction with the first and third test proteins or protein fragments.

A third chimeric gene includes a DNA sequence that encodes a third hybrid protein. The third hybrid protein contains a third test protein or protein fragment which is to be tested for interaction with the first and second proteins or protein fragments.

The interaction between the test proteins in the host cell causes the function of the amino acid sequence to be reconstituted. The method is thus carried out by introducing the chimeric genes into the host cell. The host cell is subjected to conditions under which the hybrid proteins are expressed in sufficient quantity for the function of the amino acid sequence to be reconstituted. The cells are then tested to determine whether their expression of the function of the amino acid sequence has been reconstituted to a degree greater than in the absence of the interaction of the test proteins.

In the generalized method, described above, the host cell may be any type of cell, including yeast, bacterial, or mammalian cell. The preferred host cell, however, is a bacteria cell. In carrying out this method, the first test protein may be derived from a bacterial protein in, a viral protein, an oncogene-encoded protein, a growth factor or an enzyme. The hybrid proteins may be encoded on a library of plasmids containing DNA inserts that are derived from genomic DNA, cDNA, or synthetically generated DNA sequences fused to the DNA sequence encoding the second amino acid domain.

The following example is illustrative of a preferred embodiment of the invention and is not to be construed as limiting the scope of the invention thereto.

EXAMPLE

The method and components of the kit for the present invention were tested using GAL4 as the transcriptional activator and three interacting test proteins, EGF receptor, Grb2 and Sos from the recently dissected signal transduction pathway of epidermal growth factor (EGF) stimulated mitogenesis, as reviewed by Schlessinger and Ulrich, in Neuron, 9, 383–391 (1992). The successful analysis of the pathway relies on defining components coupling the stimulated EGF receptor to Ras activation. We obtained high transcriptional activity only when all three hybrid proteins are present in the yeast cell.

The EGF receptor protein is a receptor protein for epidermal growth factor (EGF). It has been established that EGF binding to its receptor triggers tyrosine phosphorylation of the receptor cytoplasmic domain thus creating a high affinity site for binding SH2 domain (Src homology 2). The Grb2 protein (growth factor receptor bound protein 2) is an adaptor protein and contains a central SH2 domain flanked by two SH3 domains (Src homology 3). The SH2 domain of Grb2 binds to a number of tyrosine phosphorylated proteins, including autophosphorylated EGF receptor after EGF activation. See Lowenstein et al., Cell, 70, 431–442 (1992); Buday et al., Cell, 73, 611–620 (1993); Egan et al., Nature, 363, 45–52 (1993); Rozakis-Adcock, Nature, 363, 83–85 (1993); and Li et al., Nature, 363, 85–88 (1993). The Sos protein (guanine-nucleotide exchange releasing factor Son of sevenless) is a guanine-nucleotide exchange factor for Ras proteins and the SH3 domains of Grb2 binds to proline-rich motifs such as those found in the carboxyl terminal region of Sos. Thus, the EGF triggered tyrosine phosphorylation event in the EGF receptor is conveyed through Grb2 to Sos which further relays the signal by regulating the Ras activation site.

Figure 2:
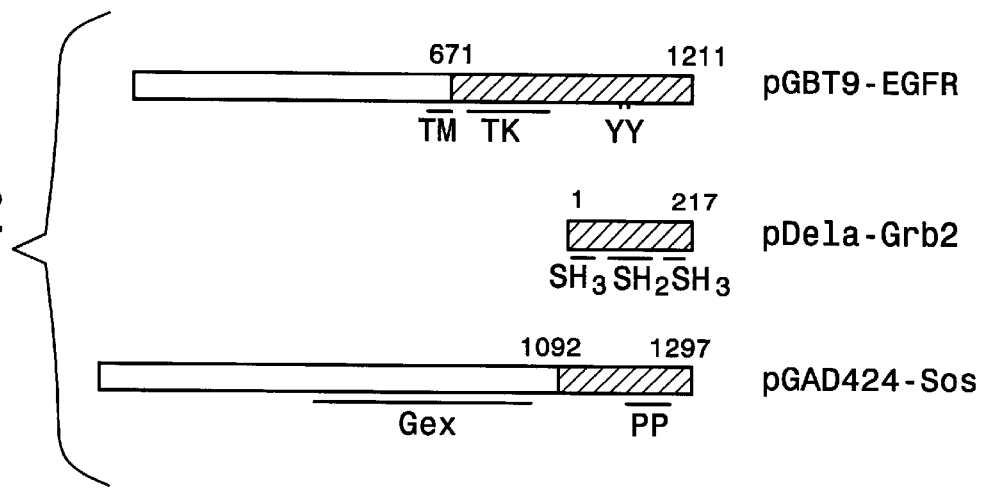
FIG. 2 is a schematic representation of three DNA fragments encoding the ternary complex of EGF receptor, Grb2 and Sos in the yeast three-hybrid system.

The constructions of the relevant portions of the plasmids used in this example are illustrated in FIG. 1 and FIG. 2. FIG. 1 is a representational map of the plasmid, pDela, for expression of a third protein-hybrid in yeast nuclei. The shuttle vector plasmid contains an Amp$^r$ gene and a Col E1 replication sequence for ampicillin-resistance selection and propagation in E. coli; a 2$\mu$ Ori replication sequence and a Ura3$^+$gene for propagation and selection in Ura$^-$ yeast strain to grow on uracil drop-out media. There are multiple cloning sites (MCS) for inserting protein of interest to be expressed in-frame as a fusion with the SV40 T antigen nuclear localization sequence (NLS) at the amino-terminus. The expression of the hybrid-protein is under the control of alcohol dehydrogenase promoter (PADH1) with cyc transcription termination sequence (T cyc1).

FIG. 2 is a schematic representation of three DNA fragments encoding the formation of detecting formation of ternary complex of EGF receptor, Grb2 and Sos in the yeast three-hybrid system. Construction of three-hybrid expressing plasmids is described below. Fragments or whole protein (filled bars) are obtained and subcloned to make pGBT9-EGFR for expressing GAL4-BD and cytoplasmic domain of EGF receptor fusion protein. Fragments or whole protein (filled bars) are obtained and subcloned to make pDela-Grb2 for expressing SV40 T antigen nuclear localization domain and Grb2 fusion protein. Fragments or whole protein (filled bars) are obtained and subcloned to make pGAD424-Sos2 for expressing GAL4-AD and carboxyl terminal domain of Sos2 fusion protein. The transmembrane domain is indicated by TM, tyrosine kinase domain is indicated by TK, the guanine-nucleotide exchange catalytic domain is indicated by Gex, and the proline rich domain is indicated by PP.

The plasmids used in this example were obtained or constructed as follows:

MATERIALS AND METHODS

The Two-hybrid System—pGAD424, pGBT9 were from Clontech (Palo Alto, Calif.). Yeast strain BY1361 (MATa, leu2-3,trpl-901, his3-200, ura3-52, ade2-101, gal4-542, gal80-538, GAL1-lacZ, GAL1-His3) was a kind gift from Dr. Jef Boeke (Johns Hopkins University School of Medicine). Growth and transformation of yeast and X-gal assay were conducted according to Clontech.

Plasmid Construction—pDela (5.6 kb) was constructed by ligating a 1.7 kb NspB II—Kpn I fragment of pGAD424 (from nucleotide 5420 to 479) and a 3.9 kb Hpa I—Kpn I fragment of pYes2 (from nucleotide 2284 to 354, pYes2 was from Invitrogen, San Diego, Calif.) in an orientation such that the two Kpn I complementary ends joined together, and the blunt end of NspB II and Hpa I joined together. The multiple cloning site region and the junction region of fragments were confirmed by DNA sequencing.

Constructs Created for the Three-hybrid Assay—The cytoplasmic domain (amino acid 671–1211) of the murine EGF receptor was obtained by reverse transcriptase and polymerase chain reactions (RT-PCR) using mouse brain mRNA. The antisense primer including a Pst I site (underlined) has the sequence of (SEQ ID NO: 1) 5' CCC CTG CAG TCA TGC TCC AAT AAA CTC ACT GC3'. The sense primer including a Sma I site has a sequence of (SEQ ID NO: 2) 5' T CCC CCG GGG CGA AGA CGT CAC ATT GTT CGA AA3'. The amplified fragment was cloned into the Sma I/Pst I sites of pGBT9 to create pGBP9-EGFR. Murine Grb2 was obtained by RT-PCR using mouse brain mRNA. The antisense primer including an EcoRI site has the sequence of (SEQ ID NO: 3) 5' G GAA TTC TTA GAC GTT CCG GTT CAC TGG G3'. The sense primer including a site BamH I had a sequence of (SEQ ID NO: 4) 5' CG GGA TCC GAA GCC ATC GCC AAA TAT GAC3'. The amplified fragment was cloned into the BamH I/EcoR I sites of pDela to create pDela-Grb2. The carboxyl terminal domain (amino acid 1092–1297) of the murine Sos2 (20) was obtained by RT-PCR using mouse brain mRNA. The antisense primer including a BamH I site had the sequence of (SEQ ID NO: 5) 5' GG GGA TCC TCA TTG AGG AGT TTT CTG CAT T3'. The sense primer including a Sma I site had a sequence of (SEQ ID NO: 6) 5' T CCC CCG GGG AAG ACT TTC TTC AGC TCA TGT3'. The amplified fragment was cloned into the Sma I/BamH I sites of pGAD424 to create pGAD424-Sos2. All inserts were verified by DNA sequencing.

These plasmids were introduced into yeast strain BY1361 (MATa, leu2-3, trpl-901, his3-200, ura3-52, ade2-101, gal4-542, gal80-538, GAL1-lacZ, GAL1-His3) which is deleted for both GAL4 and GAL80, a negative regulator of GAL4, and which also contains a GAL1-lacZ fusion gene, as described by Gill and Ptashne, in Cell, 51, 121–126 (1987). Thus β-galactosidase activity is a measure of GAL4 function derived from the plasmid-borne GAL4 constructs. The strain also contains mutations of the HIS3, LEU2 and URA3 genes, which are the selectable genes on plasmids containing the DNA-binding domain, the activation domain, and the third hybrid protein, respectively.

Transformants were grown in media which can induce transcription from $UAS_G$. The media contained 2% galactose, 2% ethanol, 2% glycerol, and did not contain either leucine or histidine, or both, as appropriate in order to maintain the plasmids.

X-gal provides the chemical color change indicating cleavage by an intact β-galactosidase. X-gal is an abbreviation for 5-bromo-4-chloro-3-indolyl-β-D-galactopyranoside. Accordingly, the yeast cells containing the interacting hybrid proteins which produced blue colonies are easily differentiated from a background of white cells containing only a single hybrid and not expressing β-galactosidase activity.

RESULTS AND DISCUSSION

In order to introduce a third-hybrid into the yeast two-hybrid system, we constructed a plasmid, pDela, which is compatible with other two-hybrid plasmids that are widely used now (FIG. 1). Most of the currently used two-hybrid plasmids, e.g. pGBT9 and pGAD424, employ $Leu^+$ and $Trp^+$ genes as selection markers for maintaining them in $leu^-$ $trp^-$ yeast strains. pDela contains a $Ura3^+$ gene so that triple transformants of pDela pGBT9- and pGAD424-plasmids can be selected on a $Ura^-Trp^-Leu^-$ yeast background. High level constitutive transcription of the third hybrid is driven by the strong promoter of house-keeping alcohol dehydrogenase gene 1 (PADH1). The third hybrid protein is targeted to yeast nuclei by the SV40 T antigen nuclear localization signal.

To validate the principles of the three-hybrid system, we used constructs of EGF receptor, Grb2 and Sos2 as an example (FIG. 2A). It is well established that EGF receptor does not contact Sos directly. But rather the phosphorylated tyrosine in EGF receptor binds to the SH2 domain in Grb2 whose SH3 domains bind Sos. Thus, a complex of EGF receptor/Grb2/Sos is formed. To test if the EGFR/Grb2/Sos complex is formed in yeast, we used a strain (BY3161) that is $Trp^-Leu^-Ura^-$ and contains reporter genes LacZ and $His3^+$ under the control of GAL4 up-stream activation sequence. When BY3161 was transformed with pGBT9-EGFR, pDela-Grb2 and pGAD424-Sos2, triple transformants expressed β-galactosidase which was detected by X-gal assay (FIG. 2B). These results indicate that GAL4 transcription factor is functionally reconstituted in vivo as a result of complex formation involving the cytoplasmic domain of EGF receptor, Grb2, and the carboxyl terminal region of Sos2. This ternary complex required all the three components because substitute any of the hybrid plasmid with its no-insert counterpart abolished the β-galactosidase activity and the growth of yeasts on histidine media. No direct interaction between the cytoplasmic domain of EGF receptor and the carboxyl terminal region of Sos occurred, demonstrating the specificities of the interactions. Expression of the third hybrid of Grb2 in nuclei is apparently crucial in mediating complex assembly.

Using the EGF receptor/Grb2/Sos2 as model, we show the yeast two-hybrid system can be expanded to include a third hybrid for detecting ternary complex formation. The three-hybrid system confirms previous in vitro co-immunoprecipitation studies showing EGF receptor/Grb2/Sos2 complex formation upon EGF activation (Lowenstein et al., Cell, 70, 431–442 (1992); Buday et al., Cell, 73, 611–620 (1993); Li et al., Nature, 363, 85–88 (1993)). Since yeast provides an environment closely mimicing in vivo situation, this result strongly supports the notion that in EGF stimulation cells, the signal is transduced via EGF receptor/Grb2/Sos complex to Ras activation.

The invention being thus described, it will be obvious that the same may be varied in many ways. Such variations are not to be regarded as a departure from the spirit and scope of the invention and all such modifications are intended to be included within the scope of the following claims.

We claim:

1. A method for screening a library for peptides or proteins that will facilitate multiple protein interactions by detecting multiple protein interactions, the method comprising:

(a) providing a yeast or mammalian host cell which is deficient in at least a first selectable marker, a second selectable marker, a third selectable marker, and a fourth selectable marker, said host cell comprising a detectable gene wherein the detectable gene expresses a detectable protein when the detectable gene is activated by an amino acid sequence including a transcriptional activation domain when the transcriptional activation domain is in sufficient proximity to the detectable gene, said detectable protein being said fourth selectable marker;

(b) providing a first plasmid comprising said first selectable marker and a first chimeric gene under control of a constitutive promoter that is expressed in the host cell, the first chimeric gene comprising a DNA sequence that encodes a first hybrid protein, the first hybrid protein comprising:
  (i) a DNA-binding domain that recognizes a binding site on the detectable gene in the host cell; and
  (ii) a first test protein or fragment thereof that is to be tested for interaction with a second test protein or fragment thereof and at least one mediating test protein or fragment thereof, wherein said first test protein or fragment thereof and said second test protein or fragment thereof do not interact directly or interact only through mediation by a mediating test protein or fragment thereof;

(c) providing a second plasmid comprising said second selectable marker and a second chimeric gene under control of a constitutive promoter that is expressed in the host cell, the second chimeric gene comprising a DNA sequence that encodes a second hybrid protein, the second hybrid protein comprising:
  (i) the transcriptional activation domain; and
  (ii) the second test protein or fragment thereof that is to be tested for interaction with the first test protein or fragment thereof and with at least one mediating test protein or fragment thereof;

(d) providing a library of third plasmids comprising said third selectable marker and at least one mediating chimeric gene under control of a constitutive promoter that is expressed in the nucleus of the host cell, each mediating chimeric gene comprising a DNA sequence that encodes a mediating hybrid cytoplasmic protein, the mediating hybrid protein comprising:
  (i) a nuclear localization peptide; and
  (ii) a mediating test protein or fragment thereof that is to be tested for interaction with the first test protein or fragment thereof and the second test protein or fragment thereof;
  wherein interaction between the first test protein or fragment thereof, the second test protein or fragment thereof, and the mediating test protein or fragment thereof in the host cell causes the transcriptional activation domain to activate transcription of the detectable gene;

(e) introducing the first plasmid, the second plasmid, and a third plasmid into the host cell;

(f) subjecting the host cell to conditions under which the first hybrid protein, the second hybrid protein, and the mediating hybrid protein are expressed, each under the control of their constitutive promoter, in sufficient quantity for the detectable gene to be activated; and, (g) detecting multiple protein interactions by determining whether the detectable gene has been expressed to a degree greater than expression in a control group of yeast or mammalian host cells which do not contain said first chimeric gene, said second chimeric gene and said mediating chimeric gene.

2. The method according to claim 1, wherein the DNA-binding domain and transcriptional activation domain are derived from a transcriptional activator having separable DNA-binding and transcriptional activation domains.

3. The method according to claim 1, wherein the first test protein, the second test protein and the mediating test protein are selected from the group consisting of a bacterial protein, a viral protein, an oncogene-encoded protein, a growth factor and an enzyme.

4. The method according to claim 1, wherein the library of third plasmids contain DNA inserts derived from genomic DNA, cDNA, synthetically generated DNA or mixtures thereof.

5. The method according to claim 1, wherein the first plasmid is a pGBT9 plasmid.

6. The method according to claim 1, wherein the second plasmid is a pGAD424 plasmid.

7. The method according to claim 1, wherein the third plasmids are a pDela plasmid.

8. The method according to claim 1, wherein the first chimeric gene is integrated into the chromosome of the host cell.

9. The method according to claim 1, wherein the DNA-binding domain and the transcriptional activation domain are from different transcriptional activators.

10. The method according to claim 1, wherein at least one of the first plasmid and the second plasmid is derived from a library of plasmids containing DNA insets derived from genomic DNA, cDNA, synthetically generated DNA or mixtures thereof.

11. The method of claim 1, wherein said first selectable marker, second selectable marker, third selectable marker and fourth selectable marker are selected from the group consisting of GAL4, HIS3, TRP3, LEU2 and URA3.

12. The method of claim 1 wherein said host cell is a *Saccharomyces cerevisiae* or *Sachizosaccharomyces pombe*.

13. The method according to claim 2, wherein the DNA-binging domain and the transcriptional activation domain are selected from the group consisting of transcriptional activators GAL4, GCN4 and ADR1.

14. The method of claim 12 wherein said constitutive promoter is an alcohol dehydrogenase promoter.

15. A method for detecting an interaction between a first test protein or fragment thereof, a second test protein or fragment thereof, and a third test protein or fragment thereof, the method comprising:

(a) providing a yeast or mammalian host cell which is deficient in at least a first selectable marker, a second selectable marker, a third selectable marker and a fourth selectable marker, said host cell containing a detectable gene wherein the detectable gene expresses a detectable protein when the detectable gene is activated by an amino acid sequence including a transcriptional activation domain when the transcriptional activation domain is in sufficient proximity to the detectable gene, said detectable protein being said fourth selectable marker;

(b) providing a first plasmid comprising said first selectable marker and a chimeric gene under control of a constitutive promoter that is expressed in the host cell, the first chimeric gene comprising a DNA sequence that encodes a first hybrid protein, the first hybrid protein comprising:
  (i) a DNA-binding domain that recognizes a binding site on the detectable gene in the host cell; and
  (ii) a first test protein or fragment thereof that is to be tested for interaction with a second test protein or fragment thereof and at least one third test protein or fragment thereof, wherein said first test protein or fragment thereof and said second test protein or fragment thereof do not interact directly or interact only through mediation by said third test protein or fragment thereof;

(c) providing a second plasmid comprising said second selectable marker and a second chimeric gene under control of a constitutive promoter that is expressed in the host cell, the second chimeric gene comprising a DNA sequence that encodes a second hybrid protein, the second hybrid protein comprising:
  (i) the transcriptional activation domain; and
  (ii) a second test protein or fragment thereof that is to be tested for interaction with the first test protein or fragment thereof and the third test protein or fragment thereof;
(d) providing a library of third plasmids comprising said third selectable marker and a third chimeric gene under control of a constitutive alcohol dehydrogenase promoter that is expressed in the nucleus of the host cell, the third chimeric gene comprising a DNA sequence that encodes a third hybrid cytoplasmic protein, the third hybrid protein comprising:
  (i) a nuclear localization peptide; and
  (ii) a third test protein or fragment thereof that is to be tested for interaction with the first test protein or fragment thereof and the second test protein or fragment thereof;
  wherein interaction between the first test protein or fragment thereof, the second test protein or fragment thereof, and the third test protein or fragment thereof in the host cell causes the transcriptional activation domain to activate transcription of the detectable gene;
(e) introducing the first plasmid, the second plasmid and a third plasmid into the host cell;
(f) subjecting the host cell to conditions under which the first hybrid protein, the second hybrid protein, and the third hybrid protein are expressed, each under the control of their constitutive promoter, in sufficient quantity for the detectable gene to be activated; and,
(g) detecting an interaction between the first test protein or fragment thereof, the second test protein or fragment thereof and the third test protein or fragment thereof by determining whether the detectable gene has been expressed to a degree greater than expression in a control group of yeast or mammalian host cells which do not contain said first chimeric gene, said second chimeric gene and said third chimeric gene.

16. The method according to claim 15, wherein the DNA-binding domain and transcriptional activation domain are derived from a transcriptional activator having separable DNA-binding and transcriptional activation domains.

17. The method according to claim 15, wherein the DNA-binding domain and the transcriptional activation domain are selected from the group consisting of transcriptional activators GAL4, GCN4, and ADR1.

18. The method according to claim 15, wherein the library of third plasmids contain DNA inserts derived from genomic DNA, cDNA, synthetically generated DNA or mixtures thereof.

19. The method according to claim 15, wherein at least one of the first plasmid and the second plasmid is derived from a library of plasmids containing DNA inserts derived from genomic DNA, cDNA, synthetically generated DNA or mixtures thereof.

20. The method according to claim 15, wherein the first test protein, the second test protein and the third test protein are selected from the group consisting of a bacterial protein, a viral protein, an oncogene-encoded protein, a growth factor and an enzyme.

21. The method according to claim 15, wherein the first plasmid is a pGBT9 plasmid.

22. The method according to claim 15, wherein the second plasmid is a pGAD424 plasmid.

23. The method according to claim 15, wherein the third plasmids are a pDela plasmid.

24. The method according to claim 15, wherein the first chimeric gene is integrated into the chromosome of the host cell.

25. The method according to claim 15, wherein the DNA-binding domain and the transcriptional activation domain are from different transcriptional activators.

26. The method of claim 15, wherein said first selectable marker, second selectable marker, third selectable marker and fourth selectable marker are selected from the group consisting of GAL4, HIS3, TRP3, LEU2 and URA3.

27. The method of claim 15 wherein said host cell is a *Saccharomyces cerevisiae* or *Sachizosaccharomyces pombe*.

28. The method of claim 27 wherein said constitutive promoter is an alcohol dehydrogenase promoter.

29. A method for detecting an interaction between a first test protein, a second test protein, and a third test protein, the method comprising:
  (a) providing a *Saccharomyces cerevisiae* host cell which is deficient in at least a first selectable marker, a second selectable marker, and a third selectable marker, said host cell containing a GAL1-lacZ gene wherein the GAL1-lacZ gene expresses a β-galactosidase protein when the GAL1-lacZ gene is activated by an amino acid sequence including a transcriptional activation domain of yeast transcription factor GAL4 when the transcriptional activation domain is in sufficient proximity to the GAL1-lacZ gene, and/or a GAL1-His3 gene which is activated providing histidine-independent yeast growth;
  (b) providing a first DNA plasmid comprising the first selectable marker and a first chimeric gene under control of a constitutive alcohol dehydrogenase promoter that is expressed in the host cell, the first chimeric gene comprising a DNA sequence that encodes a first hybrid protein, the first hybrid protein comprising:
    (i) a DNA-binding domain of yeast transcription factor GAL4 that recognizes a binding site on the GAL1-lacZ gene in the host cell; and
    (ii) a first test protein or fragment thereof that is to be tested for interaction with a second test protein or fragment thereof and at least one third test protein or fragment thereof;
  (c) providing a second DNA plasmid comprising the second selectable marker and a second chimeric gene under control of a constitutive alcohol dehydrogenase promoter that is expressed in the host cell, the second chimeric gene comprising a DNA sequence that encodes a second hybrid protein, the second hybrid protein comprising:
    (i) the transcriptional activation domain; and
    (ii) a second test protein or fragment thereof that is to be tested for interaction with the first test protein or fragment thereof and the third test protein or fragment thereof, wherein said first test protein and said second test protein do not interact directly or interact only through mediation by said third test protein;
  (d) providing a library of third DNA plasmids comprising the third selectable marker and a third chimeric gene under control of a constitutive alcohol dehydrogenase promoter that is expressed in the nucleus of the host cell, the third chimeric gene comprising a DNA sequence that encodes a third hybrid cytoplasmic protein, the third hybrid protein comprising:

(i) an SV40 T antigen nuclear localization peptide sequence; and (ii) a third test protein or fragment thereof that is to be tested for interaction with the first test protein or fragment thereof and the second test protein or fragment thereof;

wherein interaction between the first test protein or fragment thereof, the second test protein or fragment thereof, and the third test protein or fragment thereof in the host cell causes the transcriptional activation domain to activate transcription of the GAL1-lacZ gene;

(e) introducing the first DNA plasmid, the second DNA plasmid, and the third DNA plasmid into the host cell;

(f) subjecting the host cell to conditions under which the first hybrid protein, the second hybrid protein, and the third hybrid protein are expressed, each under the control of an alcohol dehydrogenase promoter, in sufficient quantity for the GAL1-lacZ gene to be activated; and (g) detecting an interaction between the first test protein or fragment thereof, second test protein or fragment thereof and a third test protein or fragment thereof by determining whether the GAL1-lacZ gene has been expressed to a degree greater than expression in a control group of *Saccharomyces cerevisiae* which does not contain said first chimeric gene, said second chimeric gene and said third chimeric gene.

30. The method according to claim 29, wherein the DNA-binding domain and transcriptional activation domain are derived from a transcriptional activator having separable DNA-binding and transcriptional activation domains.

31. The method according to claim 29, wherein the DNA-binding domain and the transcriptional activation domain are selected from the group consisting of transcriptional activators GAL4, GCN4, and ADR1.

32. The method according to claim 29, wherein the library of third plasmids contain DNA inserts derived from genomic DNA, cDNA, synthetically generated DNA or mixtures thereof.

33. The method according to claim 29, wherein at least one of the first plasmid and the second plasmid is derived from a library of plasmids containing DNA inserts derived from genomic DNA, cDNA, synthetically generated DNA or mixtures thereof.

34. The method according to claim 29, wherein the first test protein, the second test protein and the mediating test protein are selected from the group consisting of a bacterial protein, a viral protein, an oncogene-encoded protein, a growth factor and an enzyme.

35. The method according to claim 29, wherein the first plasmid is a pGBT9 plasmid.

36. The method according to claim 29, wherein the second plasmid is a pGAD424 plasmid.

37. The method according to claim 29, wherein the third plasmid is a pDela plasmid.

38. The method according to claim 29, wherein the first chimeric gene is integrated into the chromosome of the host cell.

39. The method according to claim 29, wherein the DNA-binding domain and the transcriptional activation domain are from different transcriptional activators.

40. A method for screening a library of peptides or proteins or fragment thereof for peptides or proteins or fragments thereof that will disrupt multiple protein interactions by detecting disruption of an interaction between a first test protein or peptide or fragments thereof and, a second test protein or peptide or fragment thereof, by a third test protein or peptide or fragment thereof, the method comprising:

(a) providing a yeast or mammalian host cell which is deficient in at least a first selectable marker, a second selectable marker, a third selectable marker and a fourth selectable marker, said host cell containing a detectable gene wherein the detectable gene expresses a detectable protein when the detectable gene is activated by an amino acid sequence including a transcriptional activation domain when the transcriptional activation domain is in sufficient proximity to the detectable gene, said detectable protein being said fourth selectable marker;

(b) providing a first plasmid comprising said first selectable marker and a chimeric gene under control of a constitutive promoter that is expressed in the host cell, the first chimeric gene comprising a DNA sequence that encodes a first hybrid protein, the first hybrid protein comprising:

(i) a DNA-binding domain that recognizes a binding site on the detectable gene in the host cell; and (ii) a first test protein or peptide or fragment thereof that is to be tested for interaction with a second test protein or peptide or fragment thereof and at least one third test protein or peptide or fragment thereof; wherein said first protein or peptide or fragment thereof and said second test protein or peptide or fragment thereof interact directly;

(c) providing a second plasmid comprising said second selectable marker and a second chimeric gene under control of a constitutive promoter that is expressed in the host cell, the second chimeric gene comprising a DNA sequence that encodes a second hybrid protein, the second hybrid protein comprising:

(i) the transcriptional activation domain; and (ii) a second test protein or peptide or fragment thereof that is to be tested for interaction with the first test protein or peptide or fragment thereof and the third test protein or peptide or fragment thereof;

(d) providing a library of third plasmids comprising said third selectable marker and a third chimeric gene under control of a constitutive promoter that is expressed in the nucleus of the host cell, the third chimeric gene comprising a DNA sequence that encodes a third hybrid cytoplasmic protein, the third hybrid protein comprising:

(i) a nuclear localization peptide; and (ii) a third test peptide, protein or fragment thereof that is to be tested for interaction with the first test protein or peptide or fragment thereof and the second test protein or peptide or fragment thereof;

wherein interaction between the first test protein or peptide or fragment thereof, the second test protein or peptide or fragment thereof, and the third test protein or peptide or fragment thereof, in the host cell causes the disruption of the interaction between the transcriptional activation domain and the DNA binding domain and inactivation of transcription of the detectable gene;

(e) introducing the first plasmid, the second plasmid and a third plasmid into the host cell;

(f) subjecting the host cell to conditions under which the first hybrid protein, the second hybrid protein, and the third hybrid protein are expressed, each under the control of their constitutive promoter, in sufficient quantity for the detectable gene to be inactivated; and (g) detecting a disruption of the interaction between the first test protein or peptide or fragment thereof and the second test protein or peptide or fragment thereof by determining whether the detectable gene has been expressed to a lesser degree than expression in a control group of yeast or mammalian host cells which contains said first chimeric gene and said second chimeric gene but not said third chimeric gene.

41. The method of claim 40 wherein said host cell is a *Saccharomyces cerevisiae* or *Sachizosaccharomyces pombe*.

42. The method of claim 41 wherein said constitutive promoter is an alcohol dehydrogenase promoter.

43. A kit for detecting interaction between a first test protein and a second test protein where the proteins interact through mediation by one or more third proteins, the kit comprising:

(a) a container;

(b) a *Saccharomyces cerevisiae* host cell which is deficient in a first selectable marker, a second selectable marker, a third selectable marker and a fourth selectable marker, and comprises a detectable gene comprising a binding site for a DNA-binding domain of a first hybrid protein, the binding site positioned so that the detectable gene expresses a detectable protein when the detectable gene is activated by a transcriptional activation domain encoded by a second vector, activation of the detectable gene occurs when the transcriptional activation domain is in sufficient proximity to the detectable gene, the *Saccharomyces cerevisiae* host cell, by itself, being incapable of expressing a protein having a function of a first marker gene, a second marker gene, the DNA-binding domain, or the transcriptional activation domain;

(c) a first vector comprising a promoter and a transcription termination signal functionally associated with a first chimeric gene in order to direct the transcription of the first chimeric gene, the first chimeric gene includes a DNA sequence that encodes a DNA-binding domain and at least one unique restriction site for inserting a DNA sequence encoding a first test protein or protein fragment in such a manner that the first test protein is expressed as part of a hybrid protein with the DNA-binding domain, the first vector also being self-replicable in the *Saccharomyces cerevisiae* host cell, and comprising the first selectable marker, the expression of which in the *Saccharomyces cerevisiae* host cell permits selection of cells containing the first selectable marker from cells that do not contain the first selectable marker;

(d) a second vector comprising a second chimeric gone comprising a promoter and a transcription termination signal to direct transcription, the second chimeric gene further comprising a DNA sequence that encodes a transcriptional activation domain and at least one unique restriction site to insert a DNA sequence encoding a second test protein or protein fragment into the vector, such that the second test protein is expressed as part of a hybrid protein with the transcriptional activation domain, the second vector further being self-replicable in the *Saccharomyces cerevisiae* host cell and comprising the second selectable marker, the expression of which in the *Saccharomyces cerevisiae* host cell permits selection of cells containing the second selectable marker from cells that do not contain the second selectable marker; and, (e) a third vector comprising a third chimeric gene constructed on pDela, the third chimeric gene comprising a promoter and a transcription termination signal to direct transcription, the third chimeric gene comprising at least one unique restriction site to insert a DNA sequence encoding a third cytoplasmic test protein or protein fragment into the vector in such a manner that the third test protein is expressed as part of a hybrid protein, the third vector being self-replicable in the *Saccharomyces cerevisiae* host cell, and comprising a DNA sequence encoding a nuclear localization peptide, which directs the third test protein into the nucleus, and the third selectable marker, the expression of which in the host cell permits selection of cells containing the third selectable marker from cells that do not contain the third selectable marker; and, wherein said first test protein and said second test protein do not interact directly or interact only through mediation by a third test protein.

\* \* \* \* \*